United States Patent [19]
Zucherman et al.

[11] Patent Number: 6,045,552
[45] Date of Patent: Apr. 4, 2000

[54] SPINE FIXATION PLATE SYSTEM

[75] Inventors: James F. Zucherman; Ken Y. Hsu, both of San Francisco, Calif.

[73] Assignee: St. Francis Medical Technologies, Inc., Concord, Calif.

[21] Appl. No.: 09/040,632

[22] Filed: Mar. 18, 1998

[51] Int. Cl.⁷ .................................................. A61B 17/70
[52] U.S. Cl. .................... 606/61; 606/69; 606/71
[58] Field of Search ................... 606/61, 69, 70, 606/71

[56] References Cited

U.S. PATENT DOCUMENTS

| | | | |
|---|---|---|---|
| 2,133,859 | 10/1938 | Hawley ........................ | 606/69 |
| 3,955,567 | 5/1976 | Richmond et al. ............ | 606/69 |
| 4,503,848 | 3/1985 | Casper et al. . | |
| 4,696,290 | 9/1987 | Steffee . | |
| 4,800,874 | 1/1989 | David et al. . | |
| 4,867,144 | 9/1989 | Karas et al. . | |
| 4,913,134 | 4/1990 | Luque . | |
| 5,015,248 | 5/1991 | Burstein et al. ............... | 606/74 |
| 5,084,049 | 1/1992 | Asher et al. .................. | 606/61 |
| 5,147,361 | 9/1992 | Ojima et al. .................. | 606/61 |
| 5,171,279 | 12/1992 | Mathews ........................ | 623/17 |
| 5,324,290 | 6/1994 | Zdeblick et al. .............. | 606/61 |
| 5,357,983 | 10/1994 | Mathews ........................ | 128/898 |
| 5,364,399 | 11/1994 | Lowery et al. ................ | 606/69 |
| 5,395,372 | 3/1995 | Holt et al. ..................... | 606/61 |
| 5,403,316 | 4/1995 | Ashman ......................... | 606/61 |
| 5,423,826 | 6/1995 | Coates et al. ................. | 606/96 |
| 5,470,333 | 11/1995 | Ray ............................... | 606/61 |
| 5,496,322 | 3/1996 | Mathews ........................ | 606/61 |
| 5,531,745 | 7/1996 | Ray ............................... | 606/61 |
| 5,531,747 | 7/1996 | Ray ............................... | 606/61 |
| 5,545,163 | 8/1996 | Miller et al. ................... | 606/61 |
| 5,569,248 | 10/1996 | Mathews ........................ | 606/61 |
| 5,578,034 | 11/1996 | Estes ............................. | 606/61 |
| 5,584,831 | 12/1996 | McKay ........................... | 606/61 |

OTHER PUBLICATIONS

ZPLATE Anterior Fixation Systems Surgical Technique, Sofamor Danek, rev. May 1995, 34 pgs.
The Titanium Anterior Thoracolumbar Locking Plate System, Technique Guide, Synthes Spine, printed Apr. 1994, 16 pgs.
Aesculap, Micro, Neuro and Spine Surgery, CASPAR Instruments for Anterior Cervical Fusion, 4 pgs. (No Date).
Waldemar Link GMBH & Co., Zusatzliche Implantate und Instrumente, 1 pg. (No Date).

*Primary Examiner*—Michael Buiz
*Assistant Examiner*—David O. Reip
*Attorney, Agent, or Firm*—Fliesler, Dubb, Meyer & Lovejoy LLP

[57] ABSTRACT

A spine fixation plate apparatus 50 includes a plate 52 with one or more keels 62, 64 extending therefrom for purposes of strengthening the apparatus 50 and also for purposes of providing surfaces and regions for bone ingrowth in order to firmly position the apparatus 50 in the bone and, in particular, in a vertebra. The apparatus 50 is particularly advantageous for use in an anterior approach to the L5, S1 vertebral region of the spine in order to immobilize the L5 vertebra with respect to the S1 vertebra.

33 Claims, 15 Drawing Sheets

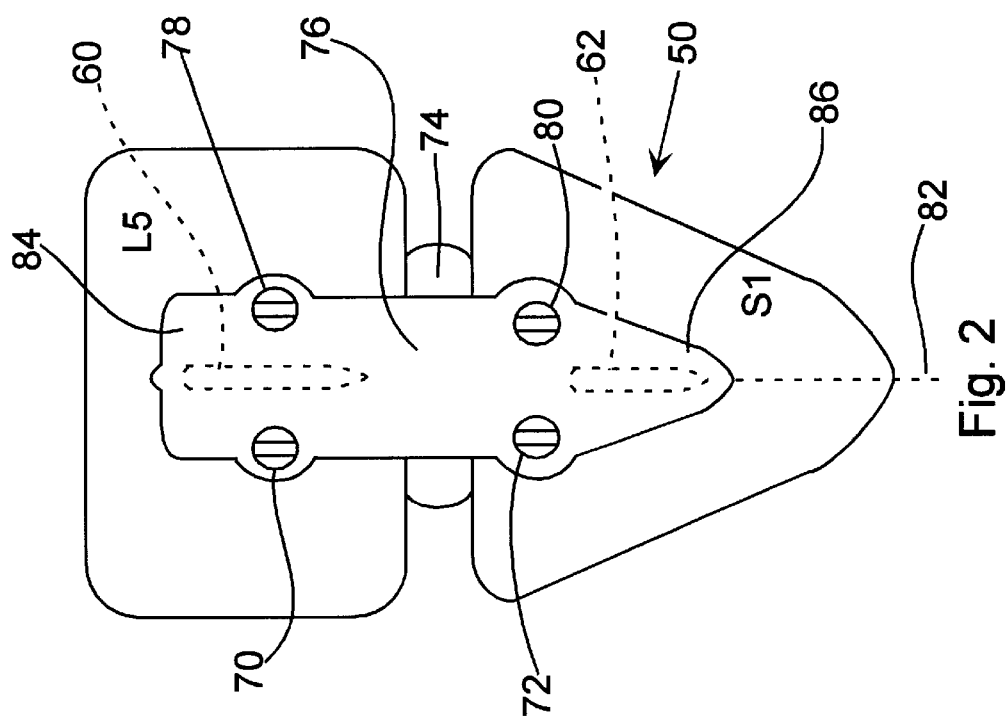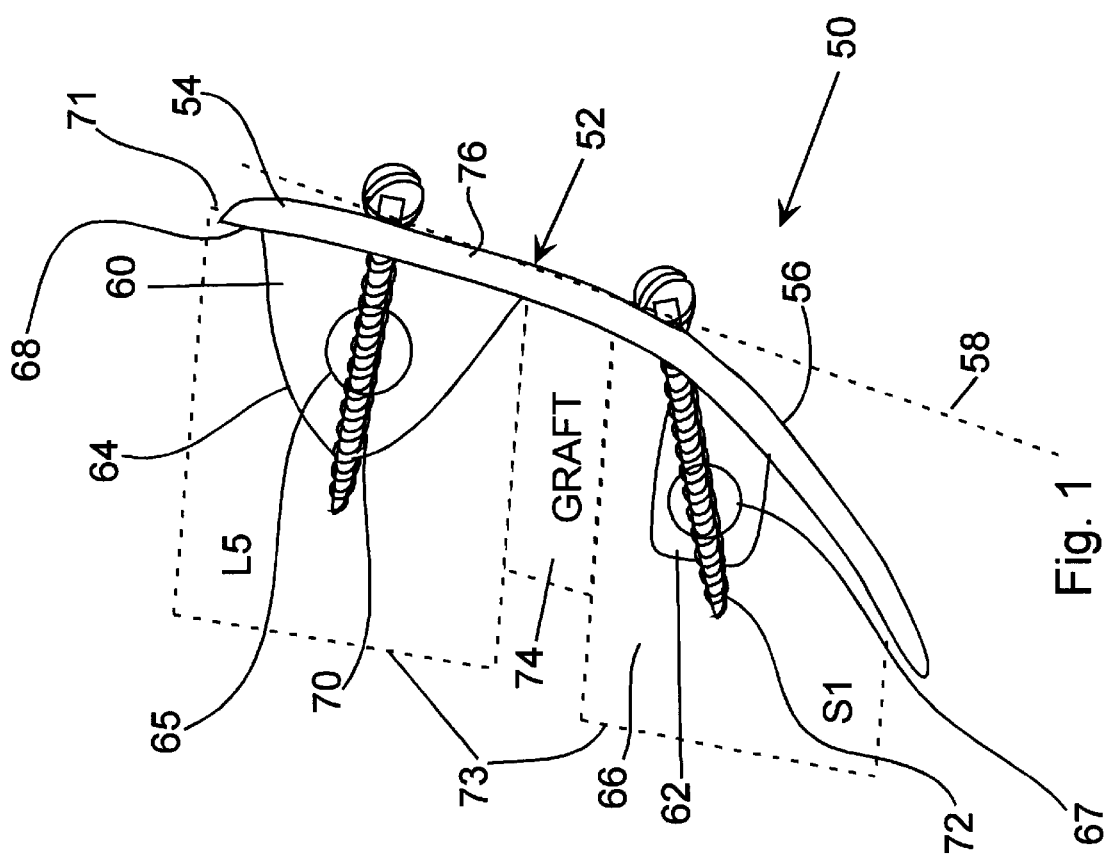

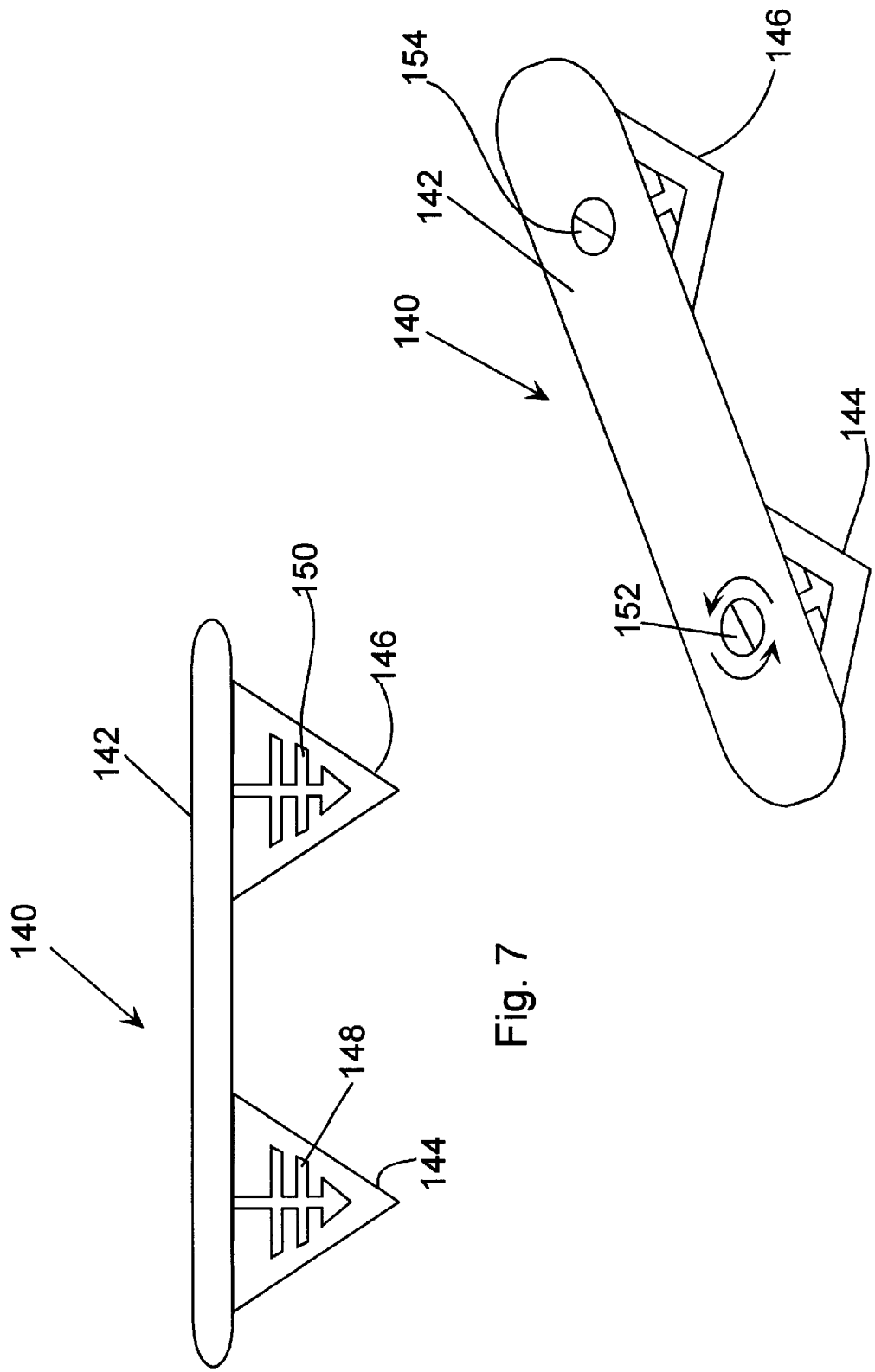

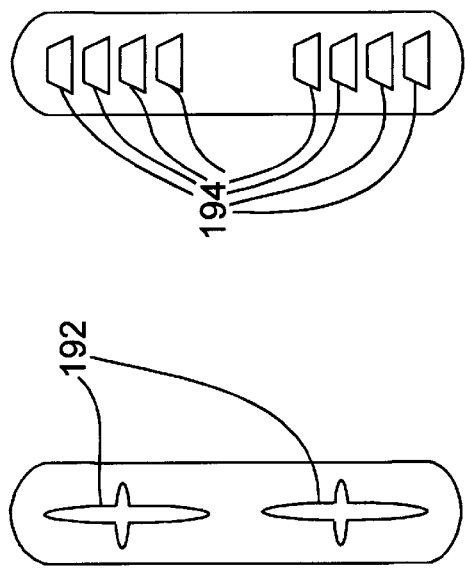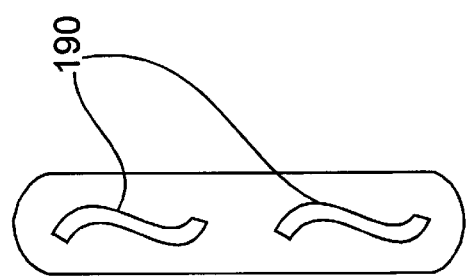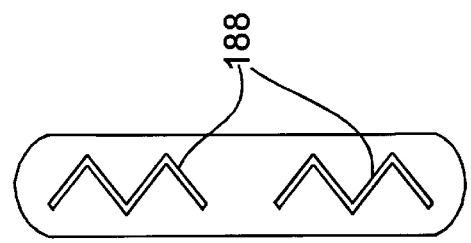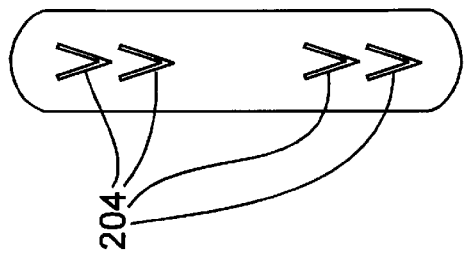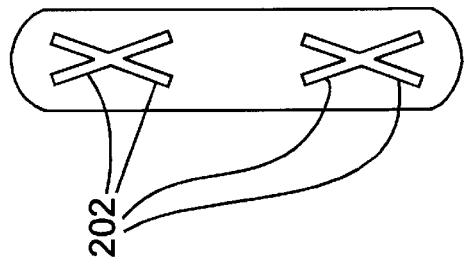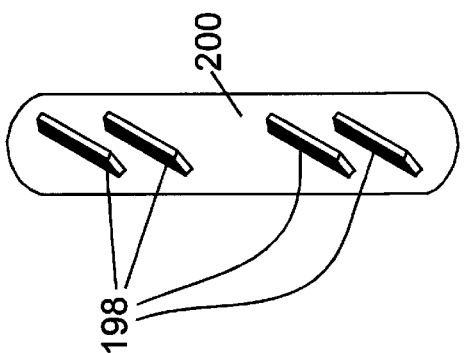

SPINE FIXATION PLATE SYSTEM

FIELD OF THE INVENTION

The present invention is related to fixation plates, and in particular, fixation plates which are applied to one or more vertebrae of a spinal column in order to immobilize and/or stabilize portions of the spinal column.

BACKGROUND OF THE INVENTION

A number of plating devices and systems are available in the art for purposes of remedying dysfunctional vertebrae and associated disks which make up the spinal column of a human or for that matter any mammal. These plating systems generally include a bar having a plurality of apertures through which can be placed screws. The screws are adapted for insertion into selected vertebral bodies. Thus, for example, a plate can be used to span a disk area in order to rigidly secure upper and lower vertebral bodies together, and/or the plate can span an entire vertebral body in order to rigidly secure a vertebral body located above the spanned vertebral body to a vertebral body located below the spanned vertebral body. In order to stabilize the spine, pairs of plating systems can be placed on opposite lateral sides of upper and lower vertebral bodies, which bracket an intermediate vertebral body. Lateral attachment methodologies are preferred due to the complication associated with both anterior and posterior approaches. Further, difficulty has been experienced with stabilizing vertebrae in the lower lumbar and upper sacrum region, and in particular, stabilizing the L5 and S1 vertebrae.

SUMMARY OF THE INVENTION

Accordingly, the presently invention is directed to a spine fixation plating system which overcomes the problems and design of the prior art.

Preferably, the spine fixation plating apparatus of the present invention is used for immobilizing a first vertebra relative to a second vertebra. The spine fixation plating apparatus includes a plate with a first plate portion adapted to be positioned adjacent to a first outer surface of a first vertebra and a second plating portion adapted to be positioned adjacent to a second outer surface of a second vertebra. The spine fixation plate system further includes a keel extending at an angle from said plate, with said keel adapted to penetrate into at least one of the first and second vertebra.

In another aspect of the invention, the keel extends from the first plate portion of the plate to the second plate portion of the plate.

In a further aspect of the present invention, the keel includes a first keel portion extending from the first plate portion and a second keel portion extending from the second plate portion.

In yet another aspect of the present invention, the first plate portion is disposed at less than a straight angle relative to the second plate portion, with a keel positioned in said less than a straight angle between the first plate portion and the second plate portion. Such an embodiment is appropriate for an anterior plating approach and in particular, for a plating between the L5 and S1 vertebrae.

In yet a further aspect of the present invention, a second keel is located in a second angle which is opposite to the less than a straight angle and is located between the first plate portion and the second plate portion.

In still a further aspect of the invention, the plate is separate from the keel and the plate includes keel ports. The keels are positionable through the keel ports and into engagement with the plate in order to penetrate the vertebra.

In yet another aspect of the invention, the keel is configured in order to enable it to be retained in the vertebra.

In still a further aspect of the invention, the keel is substantially perpendicular to the plate.

The method of the invention is appropriate for immobilizing a first vertebra relative to a second vertebra, and includes the steps of accessing the first and second vertebrae and making a slot in at least one of the first and second vertebrae. The method further includes inserting into the spine a spine fixation plate apparatus for immobilizing the first vertebra relative to the second vertebra, wherein the plate apparatus comprises a plate with a first plate portion adapted to be positioned adjacent to a first outer surface of the first vertebra and a second plate portion adapted to be positioned adjacent to a second outer surface of the second vertebra, and a keel extending at an angle from said plate, said keel adapted to penetrate into at least one of the first and second vertebrae.

In a further aspect of the method, the accessing step includes accessing the first and second vertebra anteriorly.

In another aspect of the method, a further step includes making a slot with a template using a guide port and a cutter which can fit through the guide port, with the guide port positioned adjacent to a vertebra, in order to penetrate the vertebra.

BRIEF DESCRIPTION OF THE FIGURES

FIG. 1 depicts a side view of an embodiment of the present invention.

FIG. 2 depicts an anterior view of the embodiment in FIG. 1 positioned on anterior surfaces of the L5 and S1 vertebrae.

FIG. 7 depicts a side view of a further embodiment of the present invention.

FIG. 8 depicts a top perspective view of the embodiment of FIG. 7.

FIGS. 16–22 depicts still further alternative keel design which can be used with any of the embodiments of the present invention.

DETAILED DESCRIPTION OF THE PREFERRED EMBODIMENT

Figure 4:
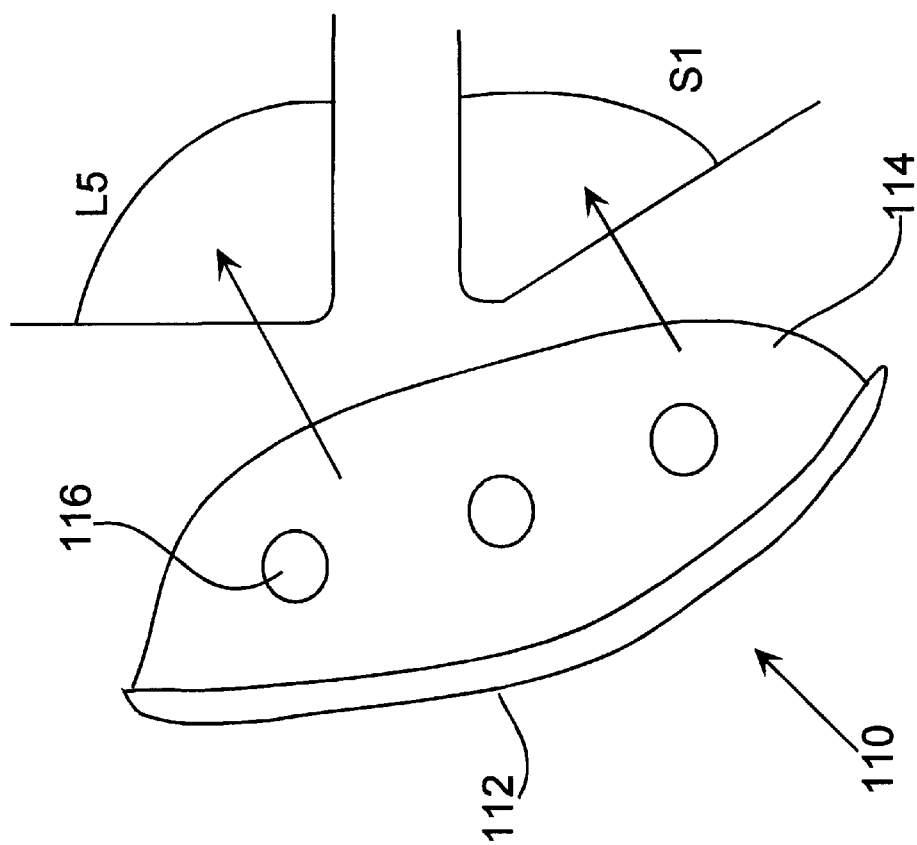
FIG. 4 depicts a side view of another embodiment of the invention.

Embodiments of FIGS. 1. 2 and 3

The first embodiment of the invention includes a spine fixation plate apparatus 50 shown in FIGS. 1 and 2. In this embodiment, the apparatus 50 include a plate 52 which has a first plate portion 54 and a second plate portion 56. As can be seen in FIG. 1, the first plate portion 54 is adapted to be located adjacent a first vertebra, which as shown in the figure, is the L5 vertebra. The second plate portion 56 is adapted to be located adjacent a second vertebra, which in FIG. 1 is the S1 vertebra. The first plate portion 54 is positioned at less than a straight angle 58 from the second plate portion 56.

The apparatus 50 further includes a first keel 60 and a second keel 62. The first keel 60 extends from the first plate portion 54, while second keel 62 extends from the second plate portion 56. In this particular embodiment, first and second keel 60, 62, are substantially perpendicular to the first and second plate portions 54, 56 respectively. It is to be understood that such keels can be disposed at angles other than perpendicular to the plate and be within the spirit and scope of the invention.

The first keel 60 additionally includes an aperture 65 and the second keel 62 includes an aperture 67. These apertures are provided in the respective keels in order to allow the vertebral bone to grow therethrough, firmly securing the apparatus 50 to the vertebrae. It is to be understood that other mechanisms such as differently shaped keels, different arrangements of apertures in the keels, and different keel surface treatments, and the like, can be utilized in order to secure the keel into the bone and provide for surfaces and contours for bone ingrowth.

As can be seen in FIG. 1, the first keel 60 is adapted to be inserted in a slot in the upper vertebra, the L5 vertebra, while the second keel 62 is designed to be inserted into the lower vertebra, in this case, the S1 vertebra. In this particular embodiment, the first keel 60 is substantially triangularly shaped, and has a sharpened edge 64. The second keel 62 is substantially rectangular and has a sharpened edge 66. Second keel 62 could also be triangularly shaped and be within the scope of the invention. Each keel extends from the posterior side 68 of the plate 52. Also depicted in FIG. 1 are first and second screws 70, 72 which are used to secure the apparatus 52 in place in the L5 and S1 vertebrae respectively.

The apparatus 50 is applied to the anterior outer surface 71 of the vertebral bodies of the L5 and S1 vertebrae and the screws are inserted into the vertebral bodies L5, S1 toward the posterior sides 73.

In this particular embodiment, it is contemplated that the keels are approximately 15 mm long so they project approximately ⅓ of the way into the vertebral body. In smaller people, the keels would be only about 10 mm–12 mm in length from the base of the keel located at the plate 52 to the tip of the keel.

As can be seen in FIG. 1, a bone graft 74 has been inserted in the disk space between the L5 and S1 vertebrae. This graft is used to fuse the L5 vertebra to the S1 vertebra, while the plate apparatus 50 immobilizes and stabilizes the L5 vertebra relative to the S1 vertebra. It is to be understood that it is possible to use other methodologies instead of a bone graft in order to fuse the vertebra together.

FIG. 2 depicts a plan view of the anterior side 76 of the plate 52. As can be seen in FIG. 2, two additional screws 78, 80, are used to secure the plate 52 to the L5 and S1 vertebrae respectfully. The screw 70, 72, 78, and 80 are inserted through apertures provided in the plate 52. Further, as is evident from FIG. 2, the plate 52 is elongated along a central longitudinal axis 82. The plate 52 also has a truncated end 84 and triangularly shaped end 86. Alternatively, the ends can also be rounded.

Figure 3:
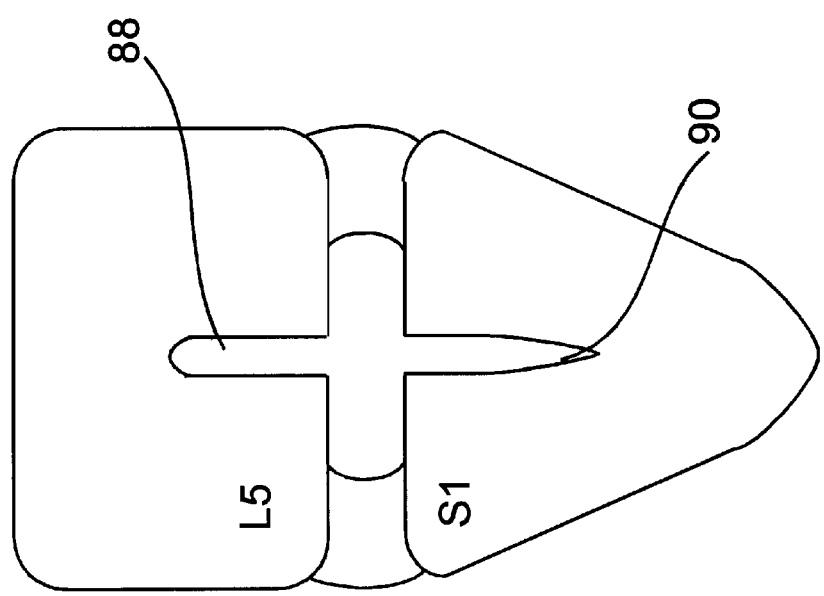
FIG. 3 depicts the L5 and S1 vertebrae prepared for receiving the embodiment of the invention of FIG. 1.

FIG. 3 depicts a site which has been prepared in the L5 and S1 vertebrae, as well as in the disk, prior to the insertion of the spine fixation plate apparatus 50 of the invention. As is evident, a first slot 88 and a second slot 90 are created in the vertebrae, and disk material is removed between the vertebrae in order to accommodate the plate apparatus 50 and a bone graft.

Figure 6:
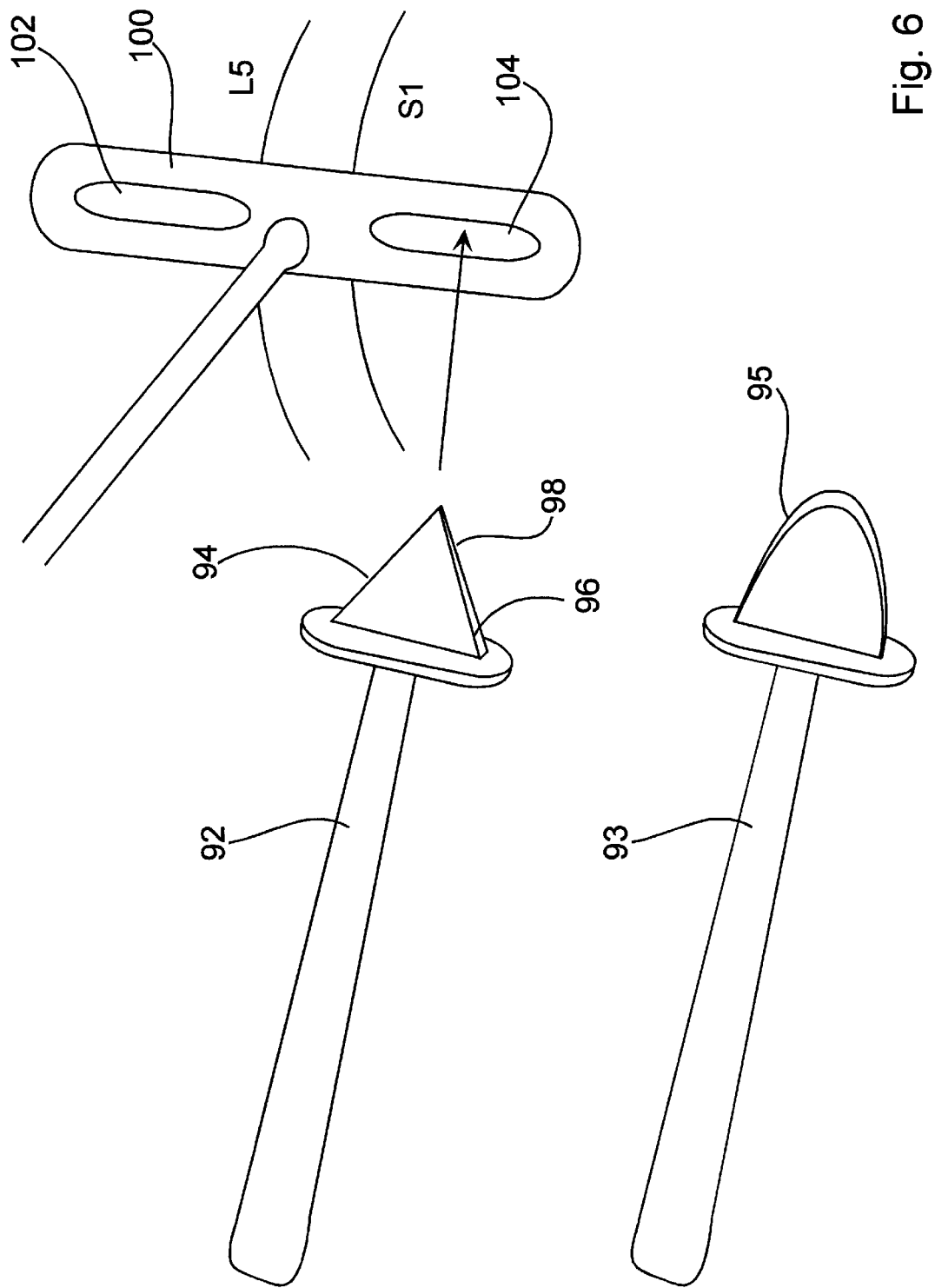
FIG. 6 depicts inventive tools for use in implanting an apparatus of the present invention.

FIG. 6 depicts instrumentation which can be used in order to make the slots 88, 90. This instrumentation includes a cutter or impacter 92, 93 which has a tip 94, 95 which is in the shape of the keel. In this particular embodiment of impactor 92, the keel is triangularly shaped and extends from a wide base 96 to a sharp point 98. Impactor 93 has a rounded tip 95 which can be used for differently shaped keels. The instrumentation for creating the slots 88, 90, also includes a template 100 which is positionable adjacent to the vertebrae, such as for example the L5 and S1 vertebrae, in order to align and locate the slots 88, 90. The template 100 includes first and second ports 102 and 104 through which the tip 94 of the cutter 92 can be inserted in order to make the slots. Once the tip 94 is inserted through the respective ports 102, 104, the impacter 92 can be, for example, hit with a mallet in order to drive the tip 94 into the bone of the vertebral body.

Embodiment of FIG. 4

Spine fixation plate apparatus 110 of FIG. 4 includes a plate 112 which is similar to plate 52 of the prior embodiment. Extending from plate 112 is a continuous keel 114 which is adapted for projection into the L5 and S1 vertebrae as well as into the disk space therebetween. The continuous keel 114 provides additional strength and integrity to the apparatus 110. In this particular embodiment, the keel 114 is substantially perpendicular to the plate 112. Further, the keel 114 includes a plurality of apertures 116 which allow for the ingrowth of vertebral bone. It is to be understood that although this and other embodiments are described with respect to the L5 and S1 vertebral bodies, that other embodiments of the invention can be designed to conform to the anatomy of different vertebral combinations and be within the spirit and scope of the invention. It is to be noted, however, that this particular embodiment, as well as the embodiment of FIGS. 1 and 2, is specially designed for anterior plating of the L5 and S1 vertebrae. Heretofore, plating of this region with an anteriorly applied plate had been undisclosed in the art. Such a plating greatly simplifies methodologies for immobilizing adjacent vertebrae and in particular the L5 and S1 vertebral pair.

Figure 5:
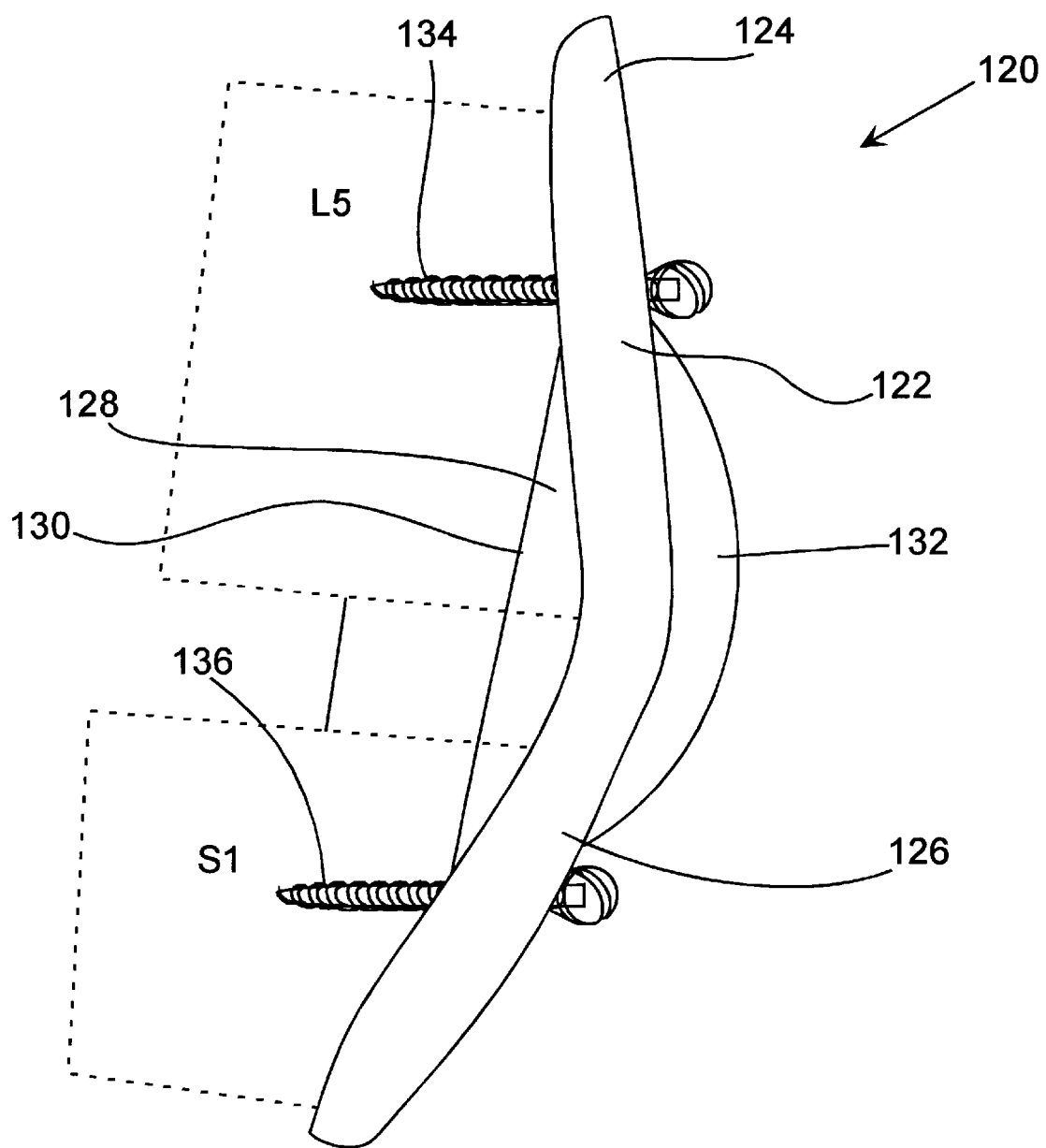
FIG. 5 depicts yet another side view of still a further embodiment of the invention.

Embodiment of FIG. 5

FIG. 5 depicts another embodiment of the spine fixation plate apparatus 120 of the invention. Apparatus 120 includes a plate 122 with upper and lower plate portions 124, 126 respectively. A keel 128 is inserted between the upper and lower plate portions 124, 126. Keel 128 is defined by line 130 which extends from the upper plate portion 124 to the lower plate portion 126. This keel 128 projects somewhat into the L5, S1 vertebrae, but not to the extent shown in FIG. 1. Keel 128 provides additional strength and integrity to the apparatus 120. In addition, a second keel 132 is disposed on the opposite side of the plate 120, projecting in a direction which is opposite to the first keel 128. Keel 128 is disposed in the less than straight angle defined between the posterior side of the upper plate portion 124 and the lower plate portion 126. Keel 132 is disposed on the opposite anterior sides of the upper and lower plate portion 124, 126, and extends in an anterior direction. Keel 132 adds additional strength and integrity to the apparatus as it extends from the upper plate portion 124 to the lower plate portion 126. Further, in order to secure the apparatus 120 to the vertebrae, screws 134 and 136 are provided.

Embodiment of FIGS. 7, 8

An embodiment of the spine fixation plate apparatus 140 of the invention is shown in FIGS. 7 and 8. Embodiment 140 includes a plate with first and second keels 144, 146, extending therefrom. These keels include a tree-shaped inserts 148, 150, respectively. In a first position, the tree-shaped inserts 148 and 150 are substantially in the plane of the first and second keels 144, 146. Upon rotation using the screw heads 152, 154, the branches of the trees 148, 150 rotate out of the plane of the keels 144, 146 in order to lock into the vertebral bone and provide more surface area and apertures for the bone to grow around and through in order to secure the keel and the apparatus to the vertebral bone.

Embodiments of FIGS. 9–22

Figure 9:
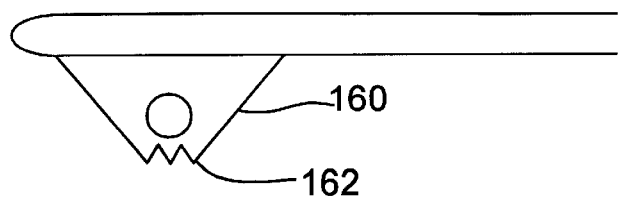
FIGS. 9–15 depict alternative keel designs which can be used with any of the embodiments of the present invention.
Figure 10:
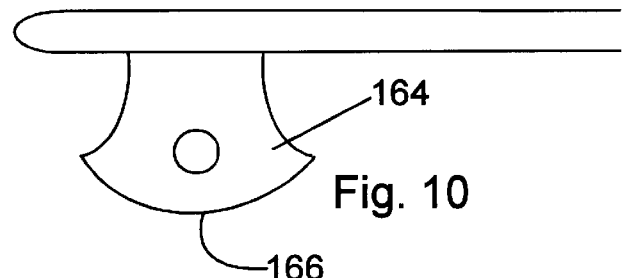
Figure 11:
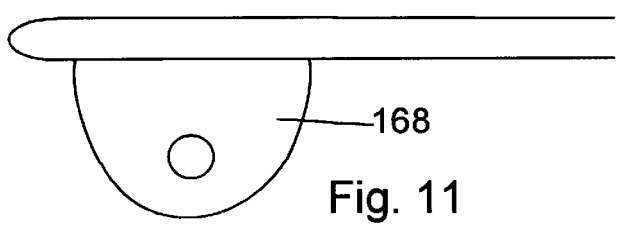
Figure 12:
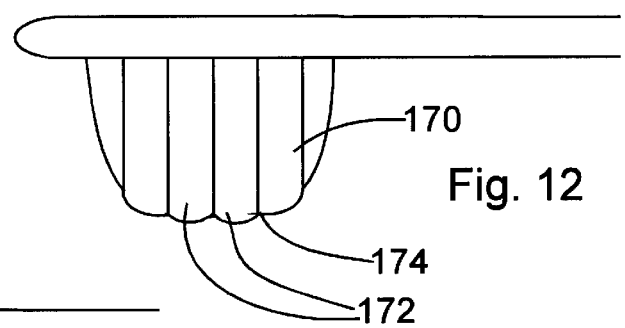
Figure 13:
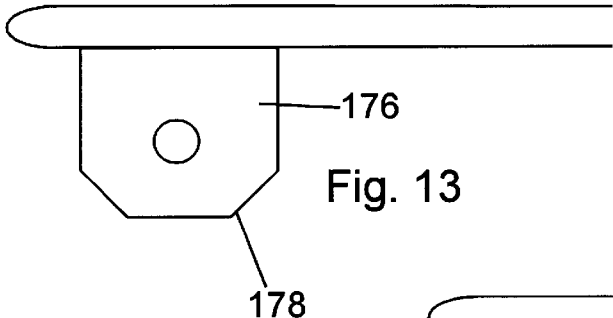

FIG. 9 depicts a modified triangularly shaped keel 160 which includes a plurality of teeth 162. Keel 164 of FIG. 10 is substantially ax-blade-shaped with a sharp leading edge 166. Keel 168 in FIG. 11 is substantially oval or circular-shaped. Keel 170 in FIG. 12 is comb-shaped with rounded projections 172 meeting in valleys 174. Keel 176 of FIG. 13 is substantially rectangularly shaped but has truncated corners, such as corner 178.

Figure 14:
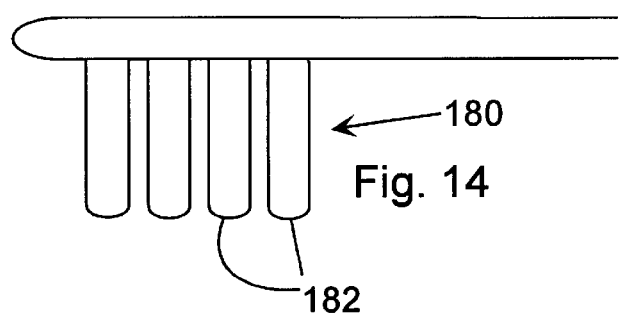
Figure 15:
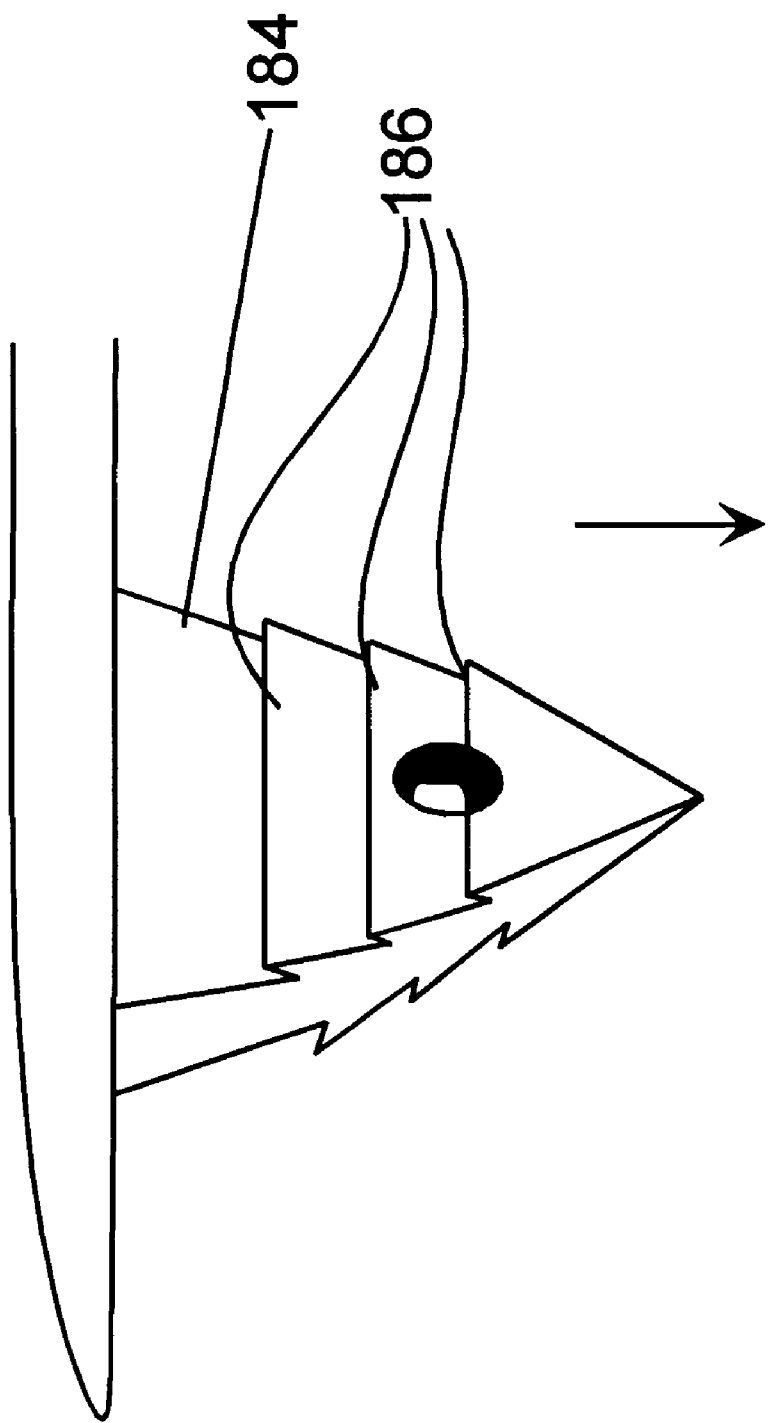

In FIG. 14, the keel 180 includes a plurality of separated elongated teeth 182. Keel 184 of FIG. 15 is substantially triangularly shaped, and includes a plurality of barbs 186, and thus cause the keel 184 to be self-locking. It is evident from the embodiment of FIG. 15, that as the keel 184 is urged into the bone, the barbs 186 prevent the keel from backing out from a final resting position. This is due to the fact that the barbs 186 bite into the bone and prevent backward movement or pullout of the keel 184 from the bone.

FIG. 16 shows a keel 188 which is substantially zig-zag shape, and which extends substantially perpendicular from the plate. The zig-zag shape adds additional strength to the keel design. Keel 190 in FIG. 17 has a substantial wave shape. Keel 192 in FIG. 18 is in the shape of a cross and is upstanding from the plate of the apparatus. In FIG. 19, the keel includes a plurality of keel portions 194 which are substantially parallel to each other and directed transverse to the longitudinal axis of the plate 196. The keel portions 194 can include any shape from FIGS. 9–15, by way of example only. Additional shapes can be developed for keel portions 194 and be within the spirit and scope of the invention.

The keel portions 198 in FIG. 20 include parallel keels which are disposed at an acute angle to the longitudinal axis of the plate 200. In FIG. 21, a keel is comprised of a plurality of keel portions 202 which are disposed in an X-shaped configuration. In FIG. 22, the keel portions 204 are clustered V-shapes or chevrons.

Figure 25:
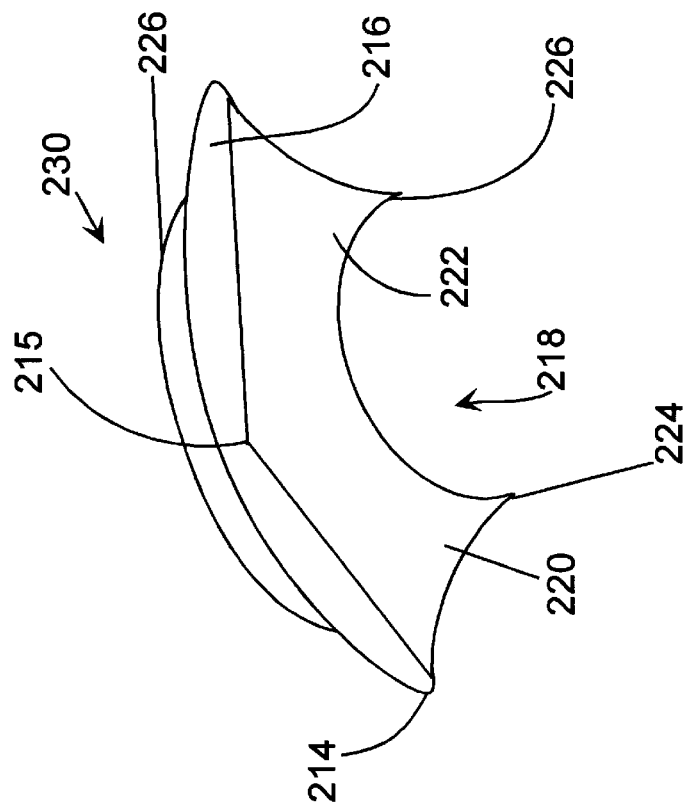
FIG. 25 depicts still a further embodiment of the present invention.
Figure 23:
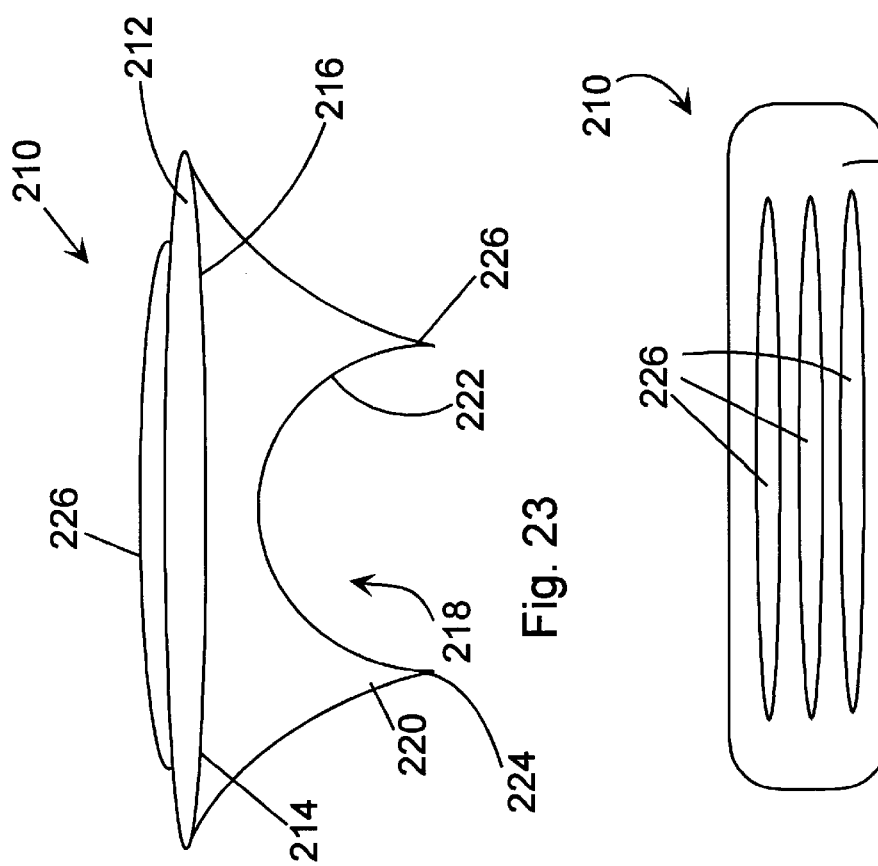
FIG. 23 depicts a side view of yet another embodiment of the present invention.
Figure 24:
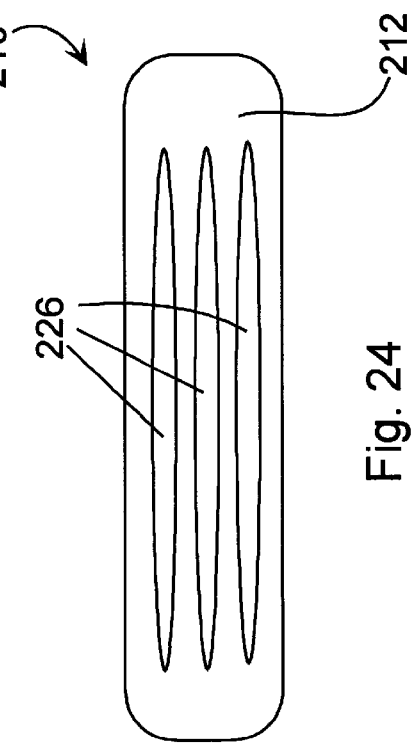
FIG. 24 depicts a top view of the embodiment of FIG. 23.

Embodiments of FIGS. 23, 24, and 25

The spine fixation plate apparatus 210 of FIGS. 23 and 24 include a plate 212, with a first plate portion 214 and a second plate portion 216. Extending from the plate 212 is a keel 218 which has first and second keel portions 220 and 222. These keel portions are essentially cusps formed by the intersection of curved edges which define the first and second keels. It is noted in FIG. 23, that the keel is continuous from the cusp 224 to cusp 226, in order to provide additional structural strength where the first plate portion 214 meets the second plate portion 216. Additionally, the embodiment 210 includes a plurality of second keels 226 (FIG. 24) which project from the anterior side of the plate 212. These keels 226 add additional strength and rigidity to the plate apparatus 210. FIG. 25 shows an embodiment 230 similar to that of FIG. 23, with similar parts having the same number. In FIG. 25, the embodiment 230 is, however, provided such that the first plate portion 214 meets the second plate portion 216 at less than a straight angle, in region 215.

Embodiments of FIGS. 26, 27, 28, 29, 30, 31, 32, and 33

Figure 26:
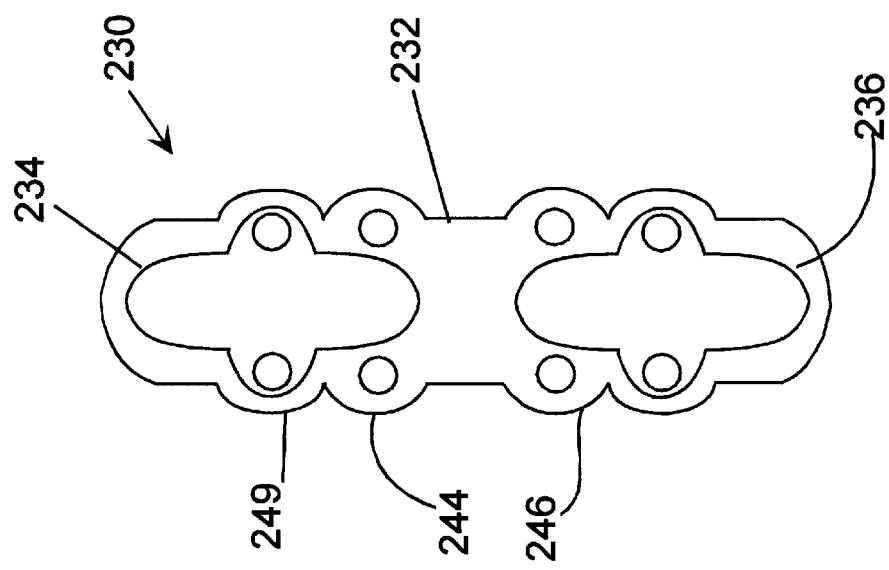
FIG. 26 depicts an anterior view of yet another embodiment of the present invention wherein the keels are removable.
Figure 31:
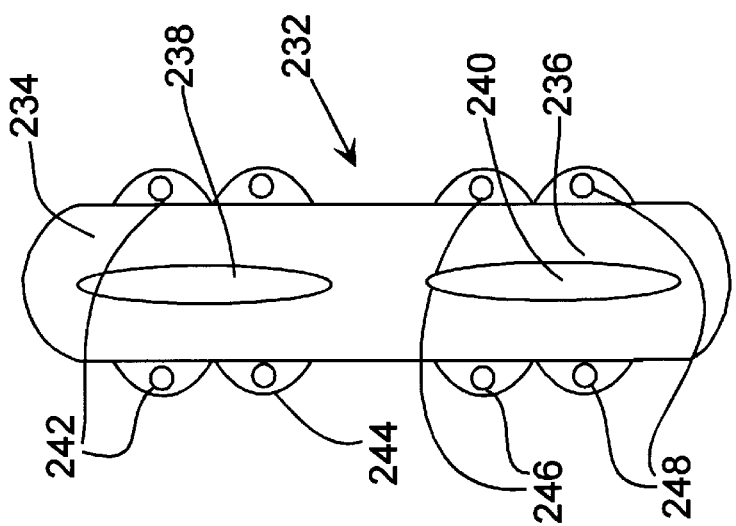
FIG. 31 depicts yet a further alternative plate which can be used with the embodiment of FIG. 26.

Another embodiment of the spine fixation plate apparatus 230 of the invention can be seen in FIG. 26. In this embodiment, a plate 232 (FIGS. 26, 31) includes a first plate portion 234 and a second plate portion 236. First plate portion 234 has provided therethrough a first keel port 238 (FIG. 31) and second plate portion 236 has provided therethrough a second keel port 240 (FIG. 31). Additionally, associated with each keel port 238, 240 are a plurality of paired apertures 242 through 248. These apertures are provided through lobes or ears which extend in pairs from the lateral sides of the plate 232. Additionally, the plate 232 in FIG. 26 is substantially flat. In a later discussion with respect to FIG. 29, a similar plate has an angular configuration, as will be discussed below, in order to accommodate, by way of example only, the L5 and S1 vertebrae.

Figure 28:
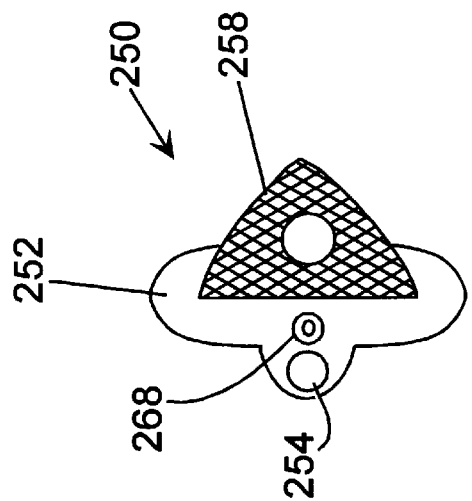
FIG. 28 depicts a posterior perspective view of the keel of FIG. 27.
Figure 27:
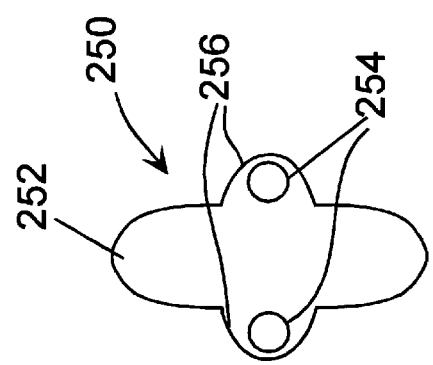
FIG. 27 depicts an anterior view of the removable keel of FIGS. 26.

FIGS. 27 and 28 depict keel 250 which includes a keel base 252 having apertures 254 provided in ears or lobes 256. Extending from the keel base 252 is the keel element 258. This keel element is like the keel in the embodiment of FIG. 1. However, it is to be understood that other keel configurations, as depicted hereinabove, can be used. In addition, it is seen that the keel element 258 has been knurled in order to roughened up the surface, providing additional surface for bone ingrowth. For implantation purposes, keels 250 are positioned in the first and second keel ports 238, 240, adjacent appropriate apertures most suitable for the particular arrangement of vertebral bodies that the keels will penetrate. In practice, the plate 234 is positioned relative to the individual slots made in the upper and lower vertebral bodies. Then, a first keel 250 is positioned through the first keel port 238 of the plate and driven into the bone. Screws are used to secure the keel and plate relative to the bone. Thereafter, the second keel 250 is inserted through a keel port 240 in the plate 232, driven into the bone, and secured with screws through the appropriate apertures in the plate 234.

Figure 29:
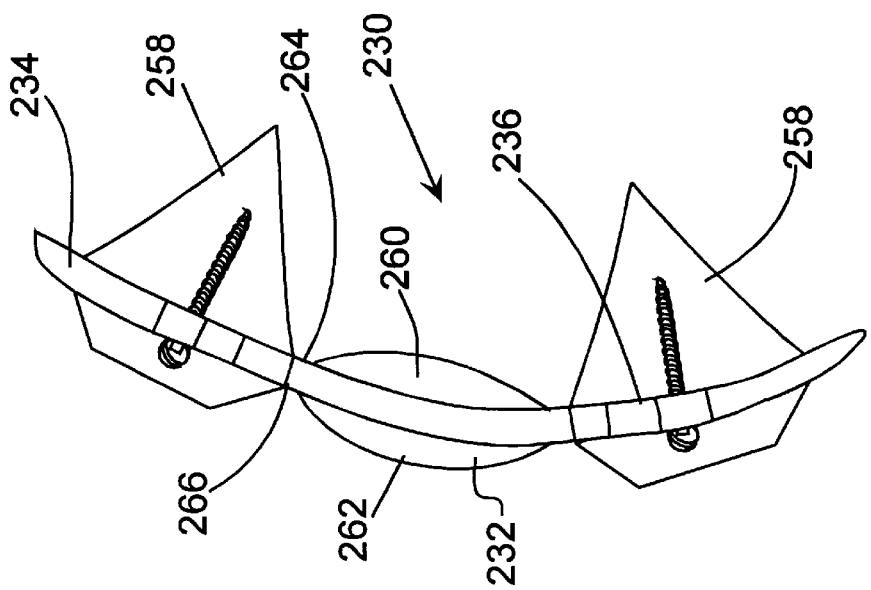
FIG. 29 depicts yet a further embodiment of the invention which has similarities to the embodiment of FIG. 26.

FIG. 29 depicts an embodiment similar to FIG. 26 except in this situation, the first plate portion 234 is disposed at an angle to the second plate portion 236. Additionally, keels or fins 260 and 262 extend from both the posterior and anterior sides 264, 266 respectively in order to strengthen the apparatus 230. In FIG. 29, screws are shown positioned through the apertures in a manner that would occur with the apparatus secured to the bone.

Figure 30:
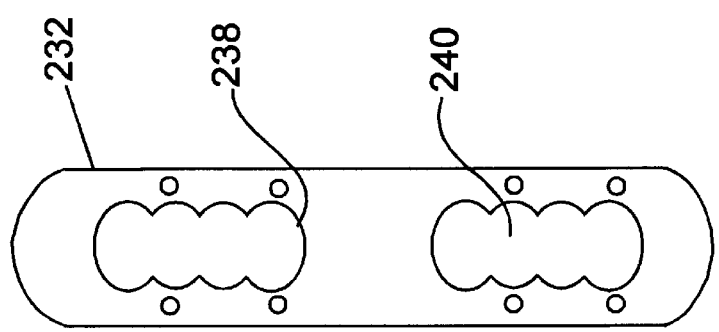
FIG. 30 depicts an alternative plate which can be used with the embodiment of FIG. 26.
Figure 33:
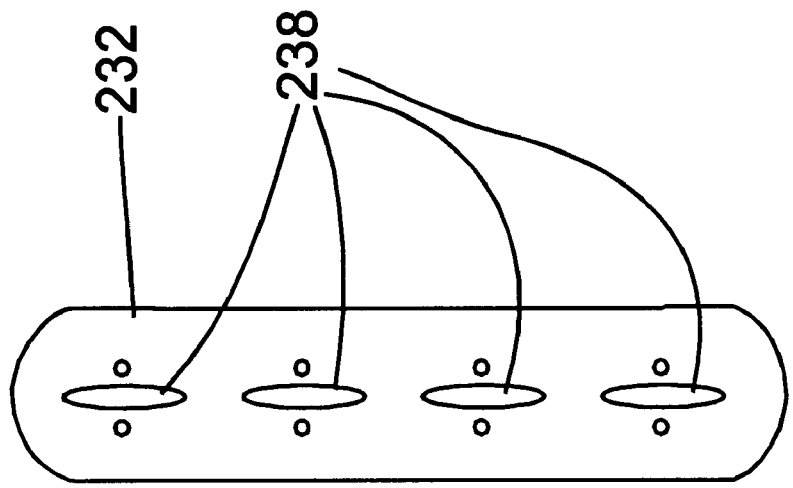
FIGS. 32 and 33 depict yet still further alternative embodiments of the plate which can be used with the embodiment of the invention of FIG. 26.
Figure 32:
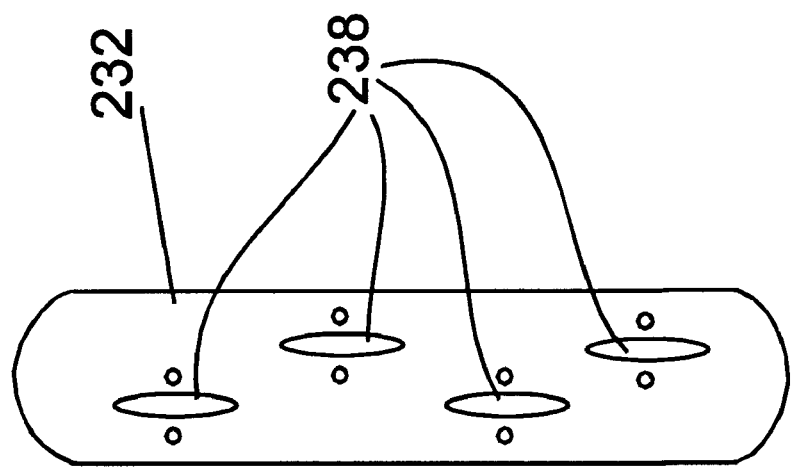

Alternative embodiments of the plate 232 are shown in FIGS. 30, 32, and 33. In FIGS. 30 and 33 the keel ports are aligned one after the other along the longitudinal axis of the plate 230. In FIG. 32 the keel ports 238 are staggered on alternate sides of the longitudinal axis of the plate 232. In FIG. 30 the keel ports 238 and 240 are scalloped in order to assist in the positioning of the individual keels 250. These scallops can receive pins such as pin 268 in the keel 250 in FIG. 28, in order to assist in the positioning of the keel 250 relative to the keel ports 238 and 240. For this other embodiment, pin 268 is omitted from keel 250 as it would interfere with the insertion of the keel into the plate.

Figure 35:
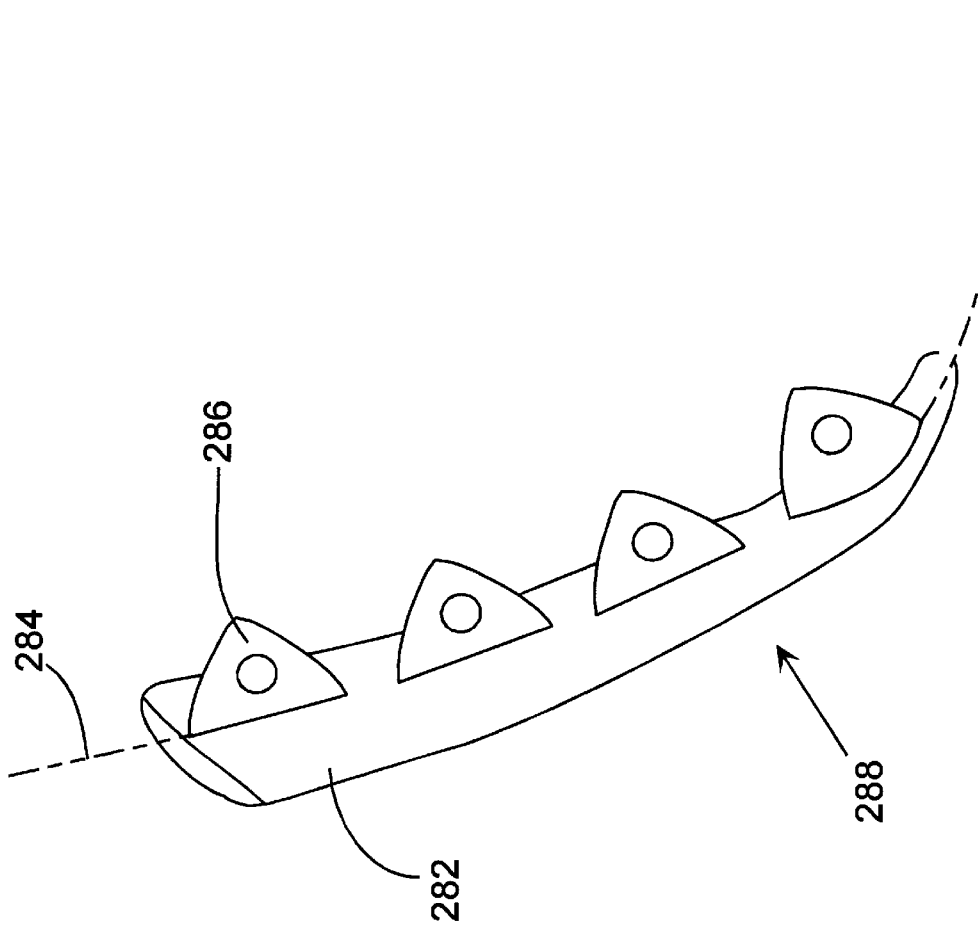
FIG. 35 depicts a perspective view of the embodiment of FIG. 34.
Figure 34:
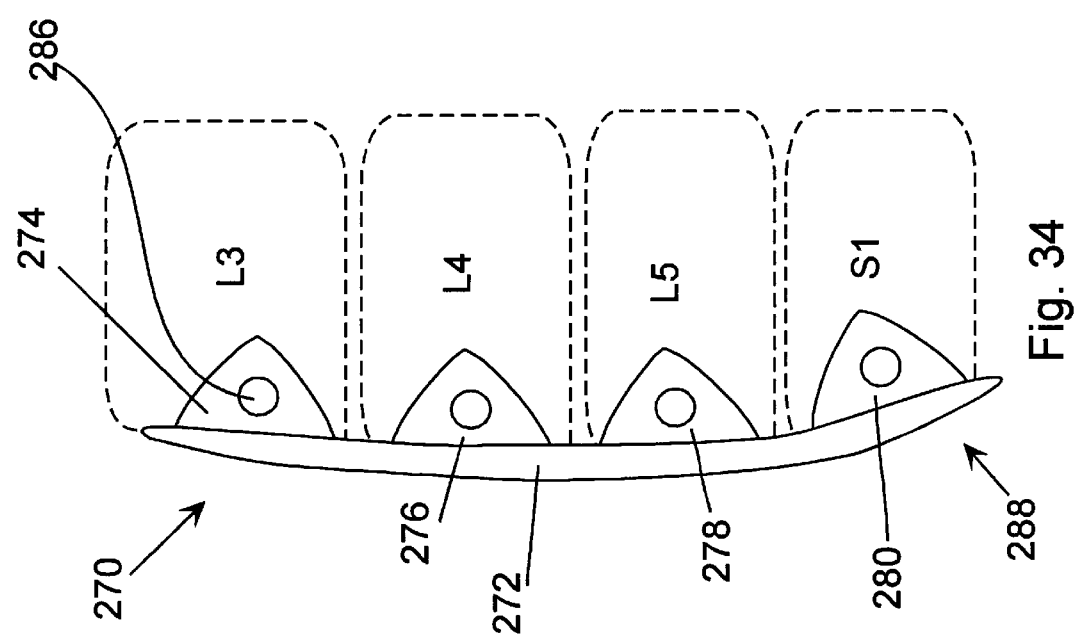
FIG. 34 depicts a side view of the embodiment of the invention which can immobilize a number of vertebrae.

Embodiments of FIG. 34 and 35

A further embodiment of the spine fixation plate apparatus 270 is shown in FIGS. 34 and 35. This embodiment 270 is designed to engage four vertebrae including the L3, L4, L5, and S1 vertebra. Other combinations of vertebrae can be chosen. As can be seen in FIG. 34, the design of this embodiment has similarities to the design of the embodiment in FIG. 1. This spine fixation plate apparatus 270 includes a plate 272 wherein four keels 274, 276, 278, and 280 extend substantially perpendicular from the posterior side 282, along a central longitudinal line 284. These keels have apertures, such as apertures 286 for purposes of promoting bone ingrowth. As with the embodiment of FIG. 1, this embodiment 270 includes a keel plate portion 288 which is specially configured to mate to the anterior outer surfaces of the L5 and S1 vertebrae.

Figure 36:
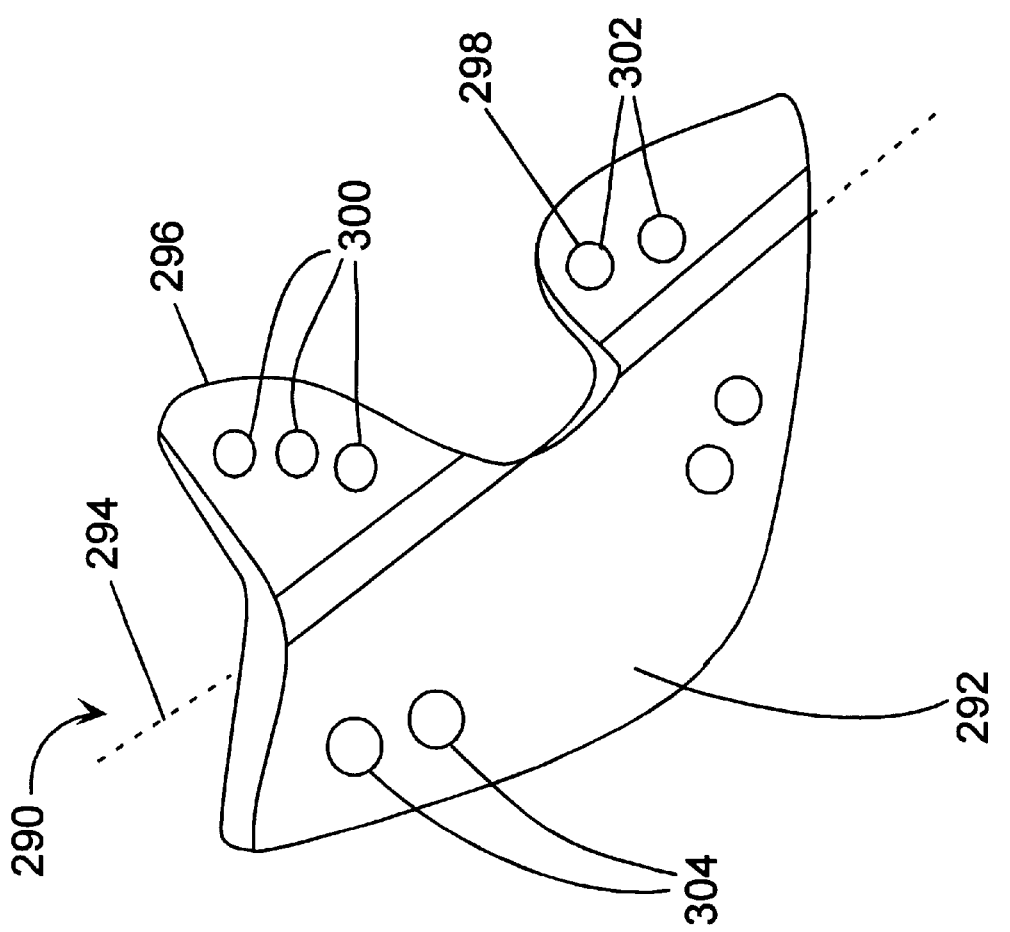
FIG. 36 depicts yet a further embodiment of the present invention.

Embodiment of FIG. 36

The spine fixation plate apparatus 290 of FIG. 36 includes a plate 292 with a longitudinal edge 294. Extending from the longitudinal edge are first and second keels 296, 298. In this embodiment, the plate 292 is approximately half the width, when measured perpendicular to the longitudinal edge 294, as is the embodiment of FIG. 1.

In the keels 296, 298 are a number of apertures 300 and 302 respectively. These apertures are for promoting bone ingrowth. Additionally, plate 292 has a plurality of apertures for purposes of accepting screws in order to screw the plate to the vertebral bodies. This particular embodiment has been configured in order to be received by the L5 and S1 vertebrae. It is to be understood that this particular embodiment 290 can be implanted by itself, or a second spine fixation plate apparatus similar to 290, but comprising a mirror image thereof, can be implanted side by side, and preferably spaced from 290, on the anterior surfaces of the L5 and S1 vertebrae.

Figure 38:
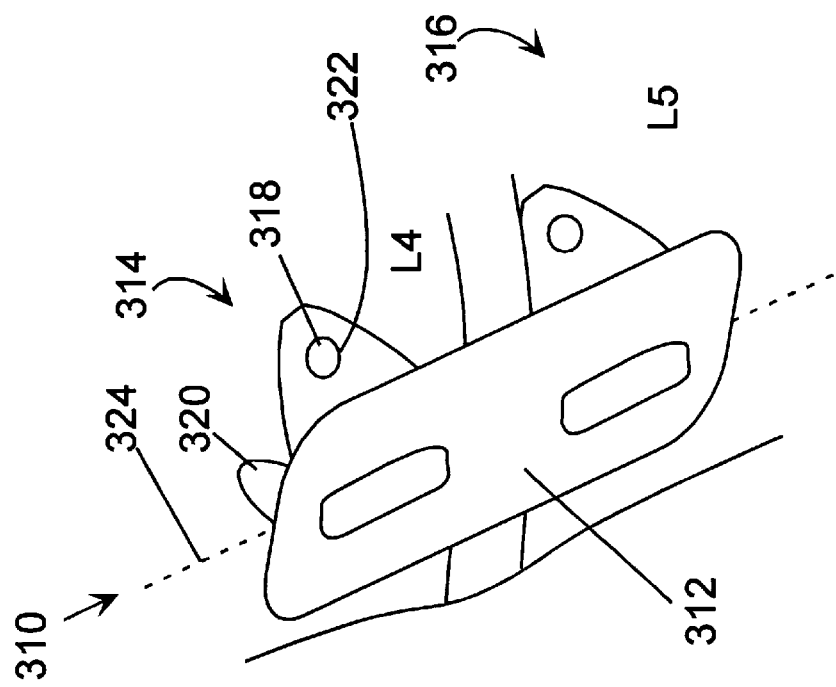
FIGS. 37 and 38 depict an end view and a perspective posterior view of yet a further embodiment of the present invention.
Figure 37:
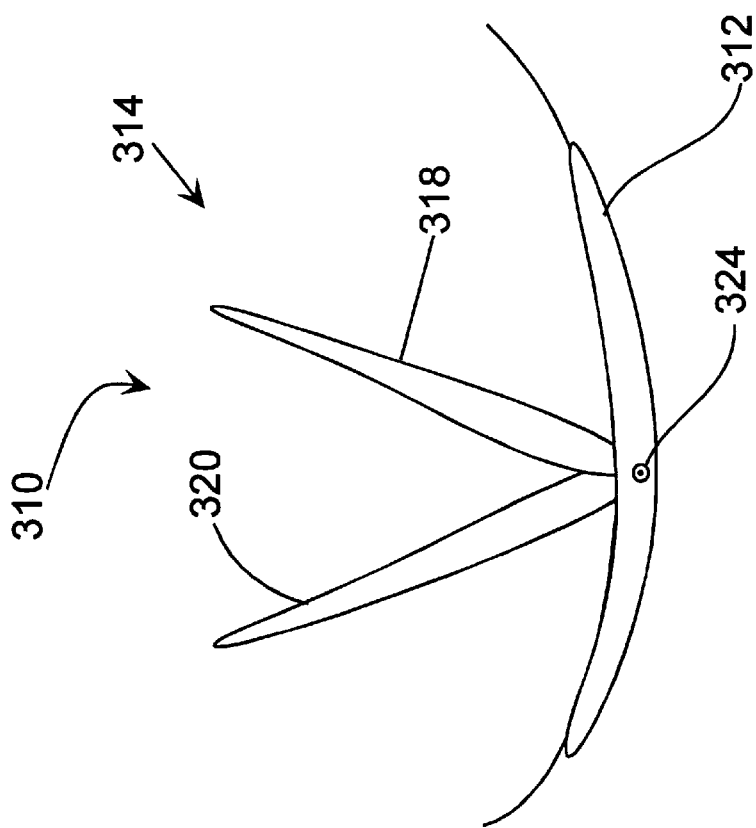

Embodiment of FIGS. 37, 38

FIGS. 37, 38 depict a further embodiment of the present invention 310, and includes a plate 312. Extending from plate 312 are keel pairs 314 and 316. Each keel pair 314, 316 includes individual keels such as keels 318, 320 which extend at less than right angles from the plate 312 and are separated from each other, in this particular embodiment, by an acute angle. Preferably, the keels 318, 320 can be somewhat flexible in order to assist in the positioning of the keels in pre-prepared slots in the vertebra. The keels include apertures 322 for purposes of promoting bone ingrowth. As can be seen in FIG. 37, the plate 312 is somewhat curved along a direction which is perpendicular to the longitudinal axis 324 in order to accommodate the shape of the anterior outer surface of the vertebra.

Industrial Applicability

The present invention, as exemplified by the above embodiments, provides a strong, lower profile, and thinner spine fixation plate apparatus and system which is particularly advantageous for anterior plating of the L5 and S1 vertebra. This apparatus and system provide for the stabilization of these vertebrae while, for example, a graft positioned between the vertebrae accepts the ingrowth of bone in order to fuse the L5 vertebra to the S1 vertebra. Such an apparatus and system is easier to insert than the multiple plating arrangements previously available and can be positioned anteriorly in a manner which is more anatomically acceptable without running into complications with respect to nerves, blood vessels, and the like.

Other features, aspects and objects of the invention can be obtained from a review of the figures and the claims.

It is to be understood that other embodiments of the invention can be developed and fall within the spirit and scope of the invention and claims.

We claim:

1. A spine fixation plate apparatus for immobilizing a first vertebra relative to a second vertebra, comprising:

a plate with a first plate portion adapted to be positioned adjacent to a first outer surface of the first vertebra and a second plate adapted to be positioned adjacent to a second outer surface of the second vertebra, said plate having a first side and a second opposite side;

a keel extending at an angle from the first side of said plate, said keel adapted to penetrate into at least one of the first and second vertebrae; and another keel positioned on the second opposite side of said plate such that the keel and the another keel extend in opposite directions.

2. The plate apparatus of claim 1 including:

said keel extending from said first plate portion of said plate to said second plate portion of said plate.

3. The plate apparatus of claim 1 including:

said keel including a first keel portion extending from said first plate portion and a second keel portion extending from said second plate portion; and wherein said first keel portion is spaced from said second keel portion.

4. The plate apparatus of claim 1 wherein:

said keel is substantially perpendicular to said plate.

5. The plate apparatus of claim 1 wherein:

said keel is sharpened in order to penetrate a vertebra.

6. The plate apparatus of claim 1 wherein:

said keel is roughened in order to be securely received in a vertebra.

7. The plate apparatus of claim 1 wherein:
said keel has ports which are adapted to receive bone which grows there through.
8. The plate apparatus of claim 1 wherein:
said keel includes means for preventing said keel from backing out once said keel is inserted in a vertebra.
9. The plate apparatus of claim 1 wherein:
said keel extends from said first plate portion to said second plate portion so that the keel is adapted to extend into the first vertebra and the second vertebra and into the disk space between the first and the second vertebrae.
10. The plate apparatus of claim 1 wherein:
said plate is adapted to span at least the first and second vertebrae and a third vertebra; and
said keel includes first, second and third keel portions which are adapted to penetrate the first, second and third vertebrae respectively.
11. The plate apparatus of claim 10 wherein the first, second and third vertebrae define a curved portion of a spinal column and wherein:
said plate is curved to accommodate the curve of the spinal column.
12. The plate apparatus of claim 1 wherein;
said plate has a longitudinal centerline; and
said keel extends from said plate from about along said centerline.
13. The plate apparatus of claim 1 wherein:
said plate has a longitudinal edge; and
said keel extends from said plate from about along said longitudinal edge.
14. A spine fixation plate apparatus for immobilizing a first vertebra relative to a second vertebra comprising:
a plate with a first plate portion adapted to be positioned adjacent to a first outer surface of the first vertebra and a second plate portion adapted to be positioned adjacent to a second outer surface of the second vertebra;
a keel extending at an angle from said plate, said keel adapted to penetrate into at least one of the first and the second vertebrae:
said first plate portion disposed at less than a straight angle of 180° relative to said second plate portion;
said less than a straight angle of 180° adapted to be positioned adjacent to first and second vertebrae; and
said keel positioned in said less than a straight angle of 180° between said first plate portion and said second plate portion so as to rigidly maintain said less than a straight angle of 180 °;
said first plate portion and said second plate portion defining a second angle opposite to said less that a straight angle of 180°, which second angle is greater than a straight angle of 180°; and
wherein a second keel is located in said second angle between the first plate portion and the second plate portion.
15. The plate apparatus of claim 14 including:
a third keel positioned adjacent to the second keel.
16. A spine fixation plate apparatus for immobilizing a first vertebra relative to a second vertebra comprising:
a plate with a first plate portion adapted to be positioned adjacent to a first outer surface of the first vertebra and a second plate portion adapted to be positioned adjacent to a second outer surface of the second vertebra;
a keel extending at an angle from said plate, said keel adapted to penetrate into at least one of the first and the second vertebrae;

said plate is separate from said keel;
said plate includes a keel port; and
said keel is insertable through said keel port into engagement with said plate, with said keel adaptively positioned so as to penetrate at least one of the first and the second vertebrae.
17. The plate apparatus of claim 16 wherein:
said keel port includes means for allowing said keel to be selectively positionable therein relative to said plate.
18. The plate apparatus of claim 16 wherein:
said keel port includes a plurality of grooves that receive said keel in a plurality of positions.
19. A spine fixation plate apparatus for immobilizing a first vertebra relative to a second vertebra comprising:
a plate with a first plate portion adapted to be positioned adjacent to a first outer surface of the first vertebra and a second plate portion adapted to be positioned adjacent to a second outer surface of the second vertebra;
a keel extending at an angle from said plate said keel adapted to penetrate into at least one of the first and the second vertebrae;
said keel includes a rotatable portion that can be rotated after said keel is positioned in a vertebra in order to secure said keel in the vertebra.
20. A spine fixation plate apparatus for immobilizing a first vertebra relative to a second vertebra comprising:
a plate with a first plate portion adapted to be positioned adjacent to a first outer surface of the first vertebra and a second plate portion adapted to be positioned adjacent to a second outer surface of the second vertebra;
a keel extending at an angle from said plate, said keel adapted to penetrate into at least one of the first and the second vertebrae;
said keel includes a rotatable portion and a non-rotatable portion, wherein said rotatable portion is initially aligned with the non-rotatable portion as the keel is inserted into a vertebrate and which rotatable portion can be rotated after said keel is positioned in a vertebra in order to secure said keel in the vertebra.
21. A spine fixation plate apparatus for immobilizing a first vertebra relative to a second vertebra comprising:
a plate with a first plate portion adapted to be positioned adjacent to a first outer surface of the first vertebra and a second plate portion adapted to be positioned adjacent to a second outer surface of the second vertebra;
a keel extending at an angle from said plate, said keel adapted to penetrate into at least one of the first and the second vertebrae;
another keel extending from said plate, which another keel is positioned along side of the keel with a major planar surface of the keel facing another major planar surface of said another keel;
said keel and said another keel are flexible; and
said keel is positioned at an acute angle with respect to said another keel.
22. A spine fixation plating system for immobilizing a first vertebra relative to a second vertebra comprising:
a plate with a first plate portion adapted to be positioned adjacent to a first outer surface of the first vertebra and a second plate portion adapted to be positioned adjacent to a second outer surface of the second vertebra;
a keel extending at a first angle from said plate, said keel adapted to penetrate into at least one of the first and the second vertebral;

said first plate portion disposed at less than a straight angle of 180° relative to said second plate portion;

said less than a straight angle of 180° adapted to be positioned adjacent to first and second vertebrae; and said keel positioned in said less than a straight angle of 180° between said first plate portion and said second plate portion so as to rigidly maintain said less than a straight angle of 180°.

23. The system of claim 22 wherein:

said keel is one piece and extends from said first plate portion to said second plate portion.

24. The system of claim 22 wherein:

said keel includes a first keel portion extending from said first plate portion and is adapted to be inserted into said first vertebra; and said keel includes a second keel portion extending from said second plate portion and is adapted to be inserted into said second vertebra.

25. The system of claim 22 wherein:

said keel is substantially perpendicular to said plate.

26. The plate apparatus of claim 22 wherein:

said plate has a longitudinal direction and a transverse direction with the keel extending in the longitudinal direction and said less than a straight angle of 180° disposed in the longitudinal direction.

27. A spine fixation plating system for immobilizing a first vertebra relative to a second vertebra comprising:

a plate with a first plate portion adapted to be positioned adjacent to a first outer surface of the first vertebra and a second plate portion adapted to be positioned adjacent to a second outer surface of the second vertebra;

a keel extending at a first angle from said plate, said keel adapted to penetrate into at least one of the first and the second vertebra;

said first plate portion disposed at less than a straight angle of 180° relative to said second plate portion;

said less than a straight angle of 180° adapted to be positioned adjacent to first and second vertebrae; and said keel positioned in said less than a straight angle of 180° between said first plate portion and said second plate portion so as to rigidly maintain said less than a straight angle of 180 °;

said plate is separate from said keel;

said plate includes a keel port; and said keel is disposable through said keel port into engagement with said plate with said keel adaptively positioned so as to penetrate at least one of the first and the second vertebrae.

28. A method of immobilizing a first vertebra relative to a second vertebra of a spine including the steps of:

accessing the first and the second vertebrae;

making a slot in at least one of the first and the second vertebrae;

inserting a spine fixation plate apparatus for immobilizing the first vertebra relative to the second vertebra wherein the plate apparatus comprises:

(a) plate with a first plate portion adapted to be positioned adjacent to a first outer surface of the first vertebra and a second plate portion adapted to be positioned adjacent to a second outer surface of the second vertebra;

(b) a keel extending at an angle from said plate, said keel adapted to penetrate into at least one of the first and the second vertebrae; and (c) said plate has a longitudinal direction extending through the first and second plate portions and a transverse direction, with said keel extending in the longitudinal direction.

29. The method of claim 28 wherein:

the accessing step includes accessing the first and second vertebrae anteriorly.

30. The method of claim 28 including the step of:

fastening the spine fixation plate apparatus to the spine with fasteners.

31. The method of claim 28 including the step of:

inserting a fusion implant between the first and the second vertebrae prior to the step of inserting the spline fixation plate apparatus.

32. A method of immobilizing a first vertebra relative to a second vertebra of a spine including the steps of:

accessing the first and the second vertebrae;

making a slot in at least one of the first and the second vertebrae;

inserting into the spine a spine fixation plate apparatus for immobilizing the first vertebra relative to the second vertebra wherein the plate apparatus comprises:

(a) plate with a first plate portion adapted to be positioned adjacent to a first outer surface of the first vertebra and a second plate portion adapted to be positioned adjacent to a second outer surface of the second vertebra;

(b) a keel extending at an angle from said plate, said keel adapted to penetrate into at least one of the first and the second vertebrae; and (c) said plate has a longitudinal direction extending through the first and second plate portions and a transverse direction, with said keel extending in the longitudinal direction;

making the slot using a template having a guide port, and a cutter which can fit through the guide port with the guide port positioned adjacent to a vertebra in order to make the slot.

33. A method of immobilizing a first vertebra relative to a second vertebra of a spine including the steps of:

accessing the first and the second vertebrae;

making a slot in at least one of the first and the second vertebrae;

inserting a spine fixation plate apparatus for immobilizing the first vertebra relative to the second vertebra wherein the plate apparatus comprises:

(a) plate with a first plate portion adapted to be positioned adjacent to a first outer surface of the first vertebra and a second plate portion adapted to be positioned adjacent to a second outer surface of the second vertebra;

(b) a keel extending at an angle from said plate, said keel adapted to penetrate into at least one of the first and the second vertebrae; and (c) said plate has a longitudinal direction extending through the first and second plate portions and a transverse direction, with said keel extending in the longitudinal direction;

said step of accessing the L5 and the S1 vertebrae includes accessing anterior surfaces of the L5 and S1 vertebrae.

* * * * *

UNITED STATES PATENT AND TRADEMARK OFFICE
CERTIFICATE OF CORRECTION

PATENT NO. : 6,045,552
DATED : April 4, 2000
INVENTOR(S) : James F. Zucherman, et al.

It is certified that error appears in the above-identified patent and that said Letters Patent is hereby corrected as shown below:

Column 9, claim 14, line 35,
delete "adjacent" and substitute
therefor --adjacent--

Column 10, claim 20, line 39,
delete "vertebrate" and substitute
therefor --vertebra--

Column 10, claim 22, line 67,
delete "vertebral" and substitute
therefor --vertebrae--

Column 12, claim 31, line 14,
delete "spline" and substitute
therefor --spine--

Signed and Sealed this

Sixth Day of March, 2001

Attest:

NICHOLAS P. GODICI

Attesting Officer    Acting Director of the United States Patent and Trademark Office